US012419925B2

(12) United States Patent
Rintola et al.

(10) Patent No.: US 12,419,925 B2
(45) **Date of Patent: *Sep. 23, 2025**

(54) FEED SUPPLEMENT

(71) Applicants: AB Vista Finland Oy, Espoo (FI); Forchem Oyj, Rauma (FI)

(72) Inventors: Mikko Rintola, Rauma (FI); Juha Orte, Rauma (FI); Juhani Vuorenmaa, Hyvinkää (FI)

(73) Assignees: AB Vista Finland Oy, Espoo (FI); Forchem Oyj, Rauma (FI)

( * ) Notice: Subject to any disclaimer, the term of this patent is extended or adjusted under 35 U.S.C. 154(b) by 505 days.

This patent is subject to a terminal disclaimer.

(21) Appl. No.: 17/588,910

(22) Filed: Jan. 31, 2022

(65) Prior Publication Data

US 2022/0152137 A1 May 19, 2022

Related U.S. Application Data

(63) Continuation of application No. 16/379,397, filed on Apr. 9, 2019, now Pat. No. 11,253,562, which is a continuation-in-part of application No. 15/035,510, filed as application No. PCT/FI2014/050832 on Nov. 5, 2014, now abandoned.

(30) Foreign Application Priority Data

Nov. 13, 2013 (FI) ..................................... 20136113

(51) Int. Cl.

| | |
|---|---|
| ***A61K 36/15*** | (2006.01) |
| ***A23K 20/10*** | (2016.01) |
| ***A23K 20/105*** | (2016.01) |
| ***A23K 20/158*** | (2016.01) |
| ***A23K 50/10*** | (2016.01) |
| ***A23L 33/10*** | (2016.01) |
| ***A61K 9/00*** | (2006.01) |
| ***A61K 31/19*** | (2006.01) |
| ***A61K 31/192*** | (2006.01) |
| ***A61K 36/00*** | (2006.01) |
| ***A61P 1/04*** | (2006.01) |

(52) U.S. Cl.

CPC .............. *A61K 36/15* (2013.01); *A23K 20/10* (2016.05); *A23K 20/105* (2016.05); *A23K 20/158* (2016.05); *A23K 50/10* (2016.05); *A23L 33/10* (2016.08); *A61K 9/0056* (2013.01); *A61K 31/19* (2013.01); *A61K 31/192* (2013.01); *A61K 36/00* (2013.01); *A61P 1/04* (2018.01); *A23V 2002/00* (2013.01); *Y02P 60/22* (2015.11)

(58) Field of Classification Search

None

See application file for complete search history.

(56) References Cited

U.S. PATENT DOCUMENTS

| | | | |
|---|---|---|---|
| 2,240,365 | A | 4/1941 | Dreger et al. |
| 2,308,431 | A | 1/1943 | Brandt |
| 2,423,236 | A | 7/1947 | Harwood et al. |
| 2,481,356 | A | 9/1949 | Segessemann et al. |
| 2,530,810 | A | 11/1950 | Christenson et al. |
| 2,611,706 | A | 9/1952 | Bernhart et al. |
| 2,736,663 | A | 2/1956 | Weber et al. |
| 2,854,420 | A | 9/1958 | Clark et al. |
| 2,866,739 | A | 12/1958 | Ciesielski et al. |
| 2,894,939 | A | 7/1959 | Hampton |
| 2,941,941 | A | 6/1960 | Groll |
| 2,987,183 | A | 6/1961 | Bishop |
| 3,001,962 | A | 9/1961 | Carlston |
| 3,009,820 | A | 11/1961 | Gould |
| 3,066,160 | A | 11/1962 | Hampton |
| 3,141,897 | A | 7/1964 | Creclius et al. |
| 3,175,916 | A | 3/1965 | Costigliola et al. |
| 3,194,728 | A | 7/1965 | Stump |
| 3,257,438 | A | 6/1966 | Wicke et al. |
| 3,311,561 | A | 3/1967 | Anderson et al. |
| 3,458,625 | A | 7/1969 | Ensor et al. |
| 3,691,211 | A | 9/1972 | Julian |
| 3,830,789 | A | 8/1974 | Garrett et al. |
| 3,887,537 | A | 6/1975 | Harada et al. |
| 3,926,936 | A | 12/1975 | Lehtinen |
| 4,000,271 | A | 12/1976 | Kremer et al. |
| 4,076,700 | A | 2/1978 | Harada et al. |
| 4,118,407 | A | 10/1978 | Red et al. |

(Continued)

FOREIGN PATENT DOCUMENTS

| | | |
|---|---|---|
| CA | 2107647 | 4/1994 |
| CN | 101461433 | 6/2009 |

(Continued)

OTHER PUBLICATIONS

Opponent's written submission to the European Patent Office for corresponding Application No. 14862579.1 mailed Aug. 1, 2022.

Bigaran et al., "Traditional Use of Conifer Resins in the Alpine Valleys of Trentino Region," La montagna che produce / Productive mountains, pp. 119-133 (2020).

Biomor Petition for Addition of DTO in National List https://www.ams.usda.gov/rules-regulations/organic/national-list/filing-petition petitions are posted in website of National Organic Program (NOP) (Nov. 30, 2008).

(Continued)

*Primary Examiner* — Jana A Hines
*Assistant Examiner* — Khatol S Shahnan Shah
(74) *Attorney, Agent, or Firm* — Merchant & Gould P.C.

(57) ABSTRACT

The present invention relates to a feed supplement or a food supplement which comprises a resin acid based composition comprising over 10% (w/w) resin acids for use in in the preven-tion of intestinal disorders. The in-vention further relates to a use of the feed supplement or the food supplement and a feed composition or a food composition comprising the feed supplement or the food supplement, respectively.

13 Claims, 4 Drawing Sheets

(56) References Cited

U.S. PATENT DOCUMENTS

| | | | | |
|---|---|---|---|---|
| 4,313,940 | A | 2/1982 | Paserela | |
| 4,437,894 | A | 3/1984 | Emerson | |
| 4,443,437 | A | 4/1984 | Prokosch et al. | |
| 4,810,299 | A | 3/1989 | Schilling et al. | |
| 4,810,534 | A | 3/1989 | Seaborne et al. | |
| 5,428,072 | A | 6/1995 | Cook et al. | |
| 5,460,648 | A | 10/1995 | Walloch et al. | |
| 5,824,322 | A | 10/1998 | Balasubramanian | |
| 6,020,377 | A | 2/2000 | O'Quinn et al. | |
| 6,229,031 | B1 | 5/2001 | Strohmaler et al. | |
| 6,608,222 | B2 | 8/2003 | Bonsignore et al. | |
| 8,741,171 | B2 | 6/2014 | Swift et al. | |
| 9,352,218 | B2 | 5/2016 | Shimamura et al. | |
| 9,358,218 | B2 * | 6/2016 | Vuorenmaa | A61K 31/19 |
| 9,422,507 | B2 | 8/2016 | Hamunen | |
| 9,789,077 | B2 | 10/2017 | Vuorenmaa et al. | |
| 9,789,143 | B2 | 10/2017 | Vuorenmaa et al. | |
| 9,907,771 | B2 | 3/2018 | Vuorenmaa et al. | |
| 9,919,013 | B2 | 3/2018 | Vuorenmaa et al. | |
| 9,962,353 | B2 | 5/2018 | Vuorenmaa | |
| 10,092,610 | B2 | 10/2018 | Vuorenmaa et al. | |
| 2002/0147356 | A1 | 10/2002 | Bonsignore | |
| 2002/0183298 | A1 | 12/2002 | Schersl et al. | |
| 2003/0144536 | A1 | 7/2003 | Sonnier et al. | |
| 2005/0107582 | A1 | 5/2005 | Wong et al. | |
| 2005/0203279 | A1 | 9/2005 | Rojas et al. | |
| 2006/0021276 | A1 | 2/2006 | Sonnier | |
| 2006/0286185 | A1 | 12/2006 | Prokosch | |
| 2008/0262045 | A1 * | 10/2008 | Eriksson | A61P 19/02 548/320.1 |
| 2008/0262251 | A1 | 10/2008 | Sato et al. | |
| 2009/0012164 | A1 | 1/2009 | Kelderman | |
| 2009/0220638 | A1 | 9/2009 | Rerez | |
| 2009/0277972 | A1 | 11/2009 | Kennon et al. | |
| 2009/0285931 | A1 | 11/2009 | Shelby et al. | |
| 2009/0297687 | A1 | 12/2009 | Marco et al. | |
| 2011/0045083 | A1 | 2/2011 | Bauer et al. | |
| 2011/0081442 | A1 | 4/2011 | Weill et al. | |
| 2011/0200570 | A1 | 8/2011 | Mosbaugh et al. | |
| 2011/0212217 | A1 | 9/2011 | Herranen et al. | |
| 2011/0212218 | A1 | 9/2011 | Herranen et al. | |
| 2012/0070516 | A1 | 3/2012 | Tranquil et al. | |
| 2013/0041192 | A1 | 2/2013 | Saviainen et al. | |
| 2013/0131007 | A1 | 5/2013 | Brown | |
| 2013/0295036 | A1 * | 11/2013 | Philippov | A61K 8/676 424/770 |
| 2015/0148416 | A1 | 5/2015 | Vuorenmaa et al. | |
| 2015/0164966 | A1 | 6/2015 | Vuorenmaa et al. | |
| 2015/0238454 | A1 | 8/2015 | Vuorenmaa et al. | |
| 2016/0081368 | A1 | 3/2016 | Vuorenmaa et al. | |
| 2016/0081952 | A1 | 3/2016 | Vuorenmaa et al. | |
| 2016/0089407 | A1 | 3/2016 | Vuorenmaa et al. | |
| 2016/0249645 | A1 | 9/2016 | Rintola et al. | |
| 2016/0250171 | A1 | 9/2016 | Vuorenmaa | |
| 2016/0250269 | A1 | 9/2016 | Rintola et al. | |
| 2016/0287650 | A1 | 10/2016 | Rintola et al. | |
| 2016/0317595 | A1 | 11/2016 | Rintola et al. | |
| 2017/0079944 | A1 | 3/2017 | Vuorenmaa et al. | |

FOREIGN PATENT DOCUMENTS

| | | | |
|---|---|---|---|
| DE | 10106078 | | 9/2002 |
| EP | 0146738 | | 7/1958 |
| EP | 0078152 | | 5/1983 |
| EP | 1586624 | | 10/2005 |
| EP | 2343061 | | 7/2011 |
| FI | 41337 | B | 6/1969 |
| FI | 20110371 | A | 4/2013 |
| FI | 20120287 | | 4/2013 |
| GB | 955316 | | 4/1964 |
| GB | 2271282 | | 4/1984 |
| GB | 2139868 | | 11/1984 |
| JP | S60237008 | | 11/1985 |
| RU | 2036589 | C1 | 6/1995 |
| WO | WO 9416690 | | 8/1994 |
| WO | WO 9910148 | | 3/1999 |
| WO | WO 02/02106 | | 1/2002 |
| WO | WO 03024681 | | 3/2003 |
| WO | WO 2006040537 | | 4/2006 |
| WO | WO 2008099051 | | 8/2008 |
| WO | WO 2008154522 | | 12/2008 |
| WO | WO 2009079680 | | 7/2009 |
| WO | WO 2009106696 | | 9/2009 |
| WO | WO 2011042613 | | 4/2011 |
| WO | WO 2011055018 | | 5/2011 |
| WO | WO 2011080399 | | 7/2011 |
| WO | WO 2011099000 | | 8/2011 |
| WO | WO 2012037297 | | 3/2012 |
| WO | WO 2013060936 | | 5/2013 |
| WO | WO 2013118099 | | 8/2013 |
| WO | WO 2013171370 | | 11/2013 |
| WO | WO 2014184430 | | 11/2014 |

OTHER PUBLICATIONS

De las Heras et al., "Terpenoids: Sources, Structure Elucidation and Therapeutic Potential in Inflammation," Current Topics in Medicinal Chemistry, vol. 3, No. 1, pp. 53-67 (2003).

European Chemical Agency ECHA Dossier—ROSIN, 6 pages.

Fernandez et al., "Anti-inflammatory activity of abletic acid, a diterpene isolated from *Pimenta racemose* var. grissea," Journal of Pharmacy and Pharmcology, vol. 53, pp. 567-872 (2001).

Kim et al., "Tetrahydroabietic Acid, a Reduced Abietic Acid, Inhibits the Production of Inflammatory Mediators in RAW264.7 Macrophages Activated with Lipopolysaccharide," J. Clin. Biochem. Nutr., vol. 46, pp. 119-125 (Mar. 2010).

Mattioli 1554.

Otto et al., "Biology and Diseases of Rats," Laboratory Animal Medicine, Third Edition, Chapter 4, pp. 151-207 (2015).

Stegelmeier et al., "The Toxic and Abortifacient Effects of Ponderosa Pine," Vet Pathol., vol. 33, No. 1, pp. 22-28 (1996).

Sunde, "The Effect of Fats and Fatty Acids in Chick Rations," Poultry Science, vol. 35, No. 2, pp. 362-368 (1955).

Who Food Additives Series: 62, "Safety evaluation of certain food additives," prepared by the Seventy-first meeting of the Joint FAO/WHO Expert Committee on Food Additives (JECFA), 292 pages (2010).

International Search Report issued in parent application PCT/FI2014/050832 completed Apr. 8, 2015.

International Preliminary Report on Patentability in PCT application PCT/FI2014/050832 with a submission date of Sep. 4, 2015.

Finnish Patent and Registration Office Action issued in parent U.S. Appl. No. 20/136,113 dated Jul. 2, 2014.

European Patent Office search report in co-pending European Patent Application 16186985.4 dated Dec. 20, 2016.

European Patent Office search report in co-pending European Patent Application 16186994.6 dated Dec. 21, 2016.

European Patent Office search report in co-pending European Patent Application 16187005.0 dated Dec. 21, 2016.

Office Action in co-pending U.S. Appl. No. 15/150,561 dated Jun. 20, 2017.

Antila, M. et al., "The fatty acids of tall oil and their ethyl and glyceryl esters as animal fodder ingredients, the chemical and physical properties of the fatty acid fraction and esters prepared from this fraction", *Journal ACTA Agricultureae Scandinavia*, 12: 95-105, 1962, Abstract.

Bannink et al., "A model of enteric fermentation in dairy cows to estimate methane emission for the Dutch National Inventory Report using the IPCC Tier 3 approach", Animal Feed Science and Technology, 166-167 (2011), pp. 603-618.

Beauchemic, K.A., et al., "Nutritional management for enteric methane abatement: a review", *Australian Journal of Experimental Agriculture*, 48: 21-27, 2008.

Bergsson et al., "Antibacterial, Antiviril and Antifungal Activities of Lipids", Lipids and Essential Oils as Antimicrobial Agents (2011), pp. 47-80.

De Graaf et al., "Consumption of tall oil-derived phytosterols in a chocolate matrix significantly decreases plasma total and low-density lipoprotein-cholesterol levels", British Journal of Nutrition (2002), 88, pp. 479-488.

(56) References Cited

OTHER PUBLICATIONS

"Carboxylic Acids, Fatty Acids from Tall Oil", Kirk-Othmer Encyclopedia of Chemical Technology, Copyright 1999-2014 by John Wiley and Sons, Inc., 4 pgs.
Duncan, "Tall Oil Fatty Acids", Naval Stores (1989), pp. 346-349.
"Explanatory Notes to the Harmonized Commodity Description and Coding System", The Department of Duty Collection of the 25 General Administration of Customs, China Commerce and TradePress, published on Jan. 31, 2007, see p. 478: "Tall Oil, Whether or Not Refined", English translation of relevant parts.
"Explanatory Notes to the Harmonized Commodity Description and Coding System", General Administration of Customs P.R. China, China Commerce and Trade Press, p. 478 (2007), Partial English Translation.
Grainger, C. et al., "Can enteric methane emissions from ruminants be lowered without lowering their production?", *Animal Feed Science and Technology*, 166-167: 308-320, 2011.
Gudmundur, B. et al., "Antibacterial, Antiviril and Antifungal Activities of Lipids" in "Lipids and Essential Oils as Antimicrobial Agents", *John Wiley & Sons*, 47-80 (2011).
Huwig et al., "Mycotoxin detoxication of animal feed by different adsorbents", Toxicology Letters, Elsevier Biomedical Press, vol. 122, Apr. 30, 2001, pp. 179-188.
Machmüller, "Medium-chain fatty acids and their potential to reduce methanogenesis in domestic ruminants", Agriculture, Ecosystems and Environment, 112 (2006) pp. 107-114.
Machmüller, A. et al., "Potential of various fatty feeds to reduce methane release from rumen fermentation in vitro (Rusitec)", *Animal Feed Science Technology*, 71: 117-130, 1998.
Magee, T. et al., "Composition of American Distilled Tall Oils", *JAOCS*, 69(4): 321-324, 1992.
McGuire et al., "Gas Chromatographic Analysis of Tall Oil Fractionation Products After Methylation with N,N-Dimethylformamide Dimethylacetal", Journal of Chromatographic Science, vol. 36, Feb. 1998, pp. 104-108.
Norlin, "Tall Oil", Ullmann's Encyclopedia of Industrial Chemistry, published online Jun. 15, 2000, pp. 583-596.
O'Quinn et al., "Effects of modified tall oil versus conjugated linoleic acid on finishing pig growth performance and carcass characteristics", Kansas Agricultural Experiment Station Research Reports, vol. 0, Issue 10, Swine Day (1968-2014), Article 723, pp. 157-161.
O'Quinn et al., "Effects of modified tall oil versus a commercial source of conjugated linoleic acid and increasing levels of modified tall oil on growth performance and carcass characteristics of growing-finishing pigs", American Society of Animal Science, (2000), pp. 2359-2368.
O'Quinn et al., "Effects of modified tall oil and creatine monohydrate on growth performance, carcass characteristics, and meat quality of growing-finishing pigs", American Society of Animal Science, 2000, pp. 2376-2382.
Patra, "Effects of Essential Oils on Rumen Fermentation, Microbial Ecology and Ruminant Production", Asian Journal of Animal and Veterinary Advances, 6(5). 2011, pp. 416-428.
Polan et al., "Biohydrogenation of Unsaturated Fatty Acids by Rumen Bacteria", Journal of Bacteriology, vol. 88, No. 4, Oct. 1946, pp. 1056-1064.
Sylfat 2LTC Product Data Sheet, Arizon Chemical, Jul. 2009.
Savluchinski-Feio et al., "Antimicrobial activity of resin acid derivatives", Applied microbiology and Biotechnology, Sep. 2006, vol. 72, No. 3, pp. 430-436.
Shetty et al., "*Saccharomyces cerevisiae* and lactic acid bacteria as potential mycotoxin decontaminating agents", Trends in Food Science & Technology, vol. 17, No. 2, Feb. 1, 2006, pp. 48-55.
Smith et al., "Isopimaric Acid from *Pinus nigra* shows Activity against Multi-drug-resistant and EMRSA Strains for *Staphylococcus aureus*", Phytotherapy Research, 19, pp. 538-542 (2005).
Snell et al., "Comparative Value of Fatty Acids and Resin Acids of Tall Oil in Soaps", American Oil Chemists' Society, vol. 27, No. 8, Aug. 1950, pp. 289-295.
Van Nevel et al., "Effect of Fatty Acid Derivatives on Rumen Methane and Propionate In Vitro[1]", Applied Microbiology, vol. 21, No. 2, Feb. 1971, pp. 365-366.
Zhou et al., "The Effect of Saturated Fatty Acids on Methanogenesis and Cell Viability of Methanobrevibacter ruminantium", Hindawi Publishing Corporation, Archaea, vol. 2013, Article ID 106916 (http://dx.doi.org/10.1155/2013/106916).
Pending Claims for U.S. Appl. No. 15/150,537 as of May 15, 2019, 2 pages.
Pending Claims for U.S. Appl. No. 15/150,555 as of May 15, 2019, 2 pages.
Indian Examination Report for corresponding Indian Patent Application No. 201617018910 mailed Feb. 4, 2020, 6 pages.
European Communication pursuant to Rule 114(2) EPC for corresponding European Patent Application No. 14862579.1 mailed Mar. 2, 2020, 17 pages.
European Communication pursuant to Rule 114(2) EPC for corresponding European Patent Application No. 16186985.4 mailed Mar. 2, 2020, 16 pages.
Emerstorfer, F. et al., "The role of plant-based antimicrobials in food and feed production with special regard to silage fermentation", Die Bodenkultur, 60(3): 55-65 (2009).
Söderberg, T. et al., "Antibacterial Activity of Rosin and Resin Acids In Vitro", Scand J Plast Reconstr Hand Surg, 24: 199-205 (1990).
Van Immerseel, F. et al., "Clostridium perfringens in poultry: an emerging threat for animal and public health", Avian Pathology, 33(6): 537-549 (2004).
Yadav, S. et al., "Strategies to modulate the intestinal microbiota and their effects on nutrient utilization, performance, and health of poultry", Journal of Animal Science and Biotechnology, 10(2): 1-11 (2019).
Pending Claims for U.S. Appl. No. 15/150,537 as of Mar. 10, 2020, 2 pages.
Pending Claims for U.S. Appl. No. 15/150,555 as of Mar. 10, 2020, 3 pages.
Communication of a Notice of Opposition for European Patent Application No. 14862579.1 dated May 14, 2021, 31 pages.
Lardo, A. et al., "Resins and gums in historical iatrosophia texts from Cyprus—a botanical and medico-pharmacological approach", Frontiers in Pharmacology, 2(32): 1-5 (Jul. 2011).
San Feliciano, A. et al., "Abietane Acids: Sources, Biological Activities, and Therapeutic Uses", Planta Med, 59: 485-490 (1993).
Shuaib, M. et al., "Pharmacognosy of Pinus roxburghii: A Review", Journal of Pharmacognosy and Phytochemistry, 2(1): 262-268 (2013).
Sipponen, A. et al., "Antimicrobial properties of natural coniferous rosin in the European Pharmacopoeia challenge test", APMIS, 119: 720-724 (2011).
Chinese Office Action for CN Application No. 2014800618534 mailed Dec. 15, 2021 (14 pages, with English translation).
Ming, "Traditional Chinese Medicine Identification Technology", Heilongjiang Science and Technology Press, 1st edition, Aug. 2013, p. 336 (3 pages).
Aguirre et al., "In-Feed Resin Acids Reduce Matrix Metalloproteinase Activity in the Ileal Mucosa of Healthy Broilers without Inducing Major Effects on the Guy Microbiota," Vet Res, 2019, 50:15, pp. 3-14.
Kettunen et al., "Resin Acid Composition Reduces Small-Intestinal Expression of Collagen-Degrading Matrix Metalloproteinases in Broilers," Poster, 2019, 1 page.
Kolpe et al., "In-Feed Resin Acids Improve Small-Intestinal Mucosal Characteristics of Broiler Chickens During Dysbiosis Challenge," Poster, 2019, 1 page.
Manicone et al., "Matrix Metalloproteinases as Modulators of Inflammation," Semin Cell Dev Bio., 2008, 19(1):34-41.
Moore et al., "Matrix Metalloproteinase-9 Inhibition Reduces Inflammation and Improves Motility in Murine Models of Postoperative Ileus," Gastroenterology, 2011, 141:1283-1292.
Parks et al., "Matrix Metalloproteinases as Modulators of Inflammation and Innate Immunity," Immunology, 2004, 4:617-629.

* cited by examiner

FEED SUPPLEMENT

CROSS-REFERENCE TO RELATED APPLICATIONS

This application is a continuation of U.S. patent application Ser. No. 16/379,397, filed Apr. 9, 2019, which is a continuation-in-part of U.S. patent application Ser. No. 15/035,510, filed 10 May 2016, now abandoned, which is a National Stage Application of PCT/FI2014/050832, filed 5 Nov. 2014, which benefit of Serial No. 20136113, filed 13 Nov. 2013 in Finland, and which applications are incorporated herein by reference. To the extent appropriate, a claim of priority is made to each of the above disclosed applications.

FIELD OF THE INVENTION

The invention relates to a method for preventing intestinal disorders.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Ruminant animals can utilize fiber-rich raw materials which have little or no nutritional value for monogastrics like the human. However, the feed conversion efficiency of ruminants is relatively low and their methane production represents a remarkable share of the world's greenhouse gas emissions. With the increasing demand of food there is a need to improve the feed conversion efficiency of ruminants and to lower their methane production. Generally, there is an increasing demand for ingredients for use in animal feeding that can modulate the microbial population in the animal digestive tract but which are readily available, well tolerated and environmentally friendly.

Fractional distillation of crude tall oil (CTO), obtained as a by-product of the Kraft process of wood pulp manufacture, produces depitched tall oil which typically comprises over 10% resin acids and less than 90% fatty acids. Further refinement of depitched tall oil produces tall oil fatty acid (TOFA), Distilled Tall Oil (DTO) and Tall Oil Rosin (TOR) which are available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

Toxins are poisonous substances produced within living cells or organisms. Toxins such as mycotoxins are a chemically variable group of secondary metabolites of fungi, which can be found in grains and other feedstuffs even in the absence of any visible fungal growth. High temperature and air humidity during the storage increase the likelihood of fungal growth, but mycotoxin contamination can also occur already in the field. Visible appearance or smell of grains or silage does not indicate the presence or absence of mycotoxin contamination. Effects of toxins such as mycotoxins to farm animals are very variable, and range from increased mortality to decreased fertility and performance. Mycotoxins may also disturb the immune system of animals and make them more susceptible to diseases.

Due to the chemical variability of mycotoxins, analysis of all feedlots for even the most common mycotoxins would be too expensive. Therefore mycotoxin adsorbents are often used to give extra insurance against mycotoxin contamination in feeds. Mycotoxin adsorbents are substances that are itself not digested or absorbed by the animal. They are assumed to bind toxins during the passage through the alimentary canal. Thus, instead of being absorbed by the animals, the toxins get eventually voided via feces.

Toxin binders can also adsorb other types of toxins, like bacterial toxins or secondary metabolites of plants from the digestive tract. Activated carbon (charcoal) is an efficient toxin binder. It is a recommended general toxin binder in various poisonings. However, charcoal also binds vitamins and minerals, which makes it unsuitable for continuous use in feeds.

PURPOSE OF THE INVENTION

The purpose of the invention is to provide a new type of feed supplement or food supplement comprising resin acid based composition for use in the prevention of intestinal disorders.

SUMMARY

The method according to the present invention is characterized by what is presented in claim 1.

DETAILED DESCRIPTION

Figure 1:
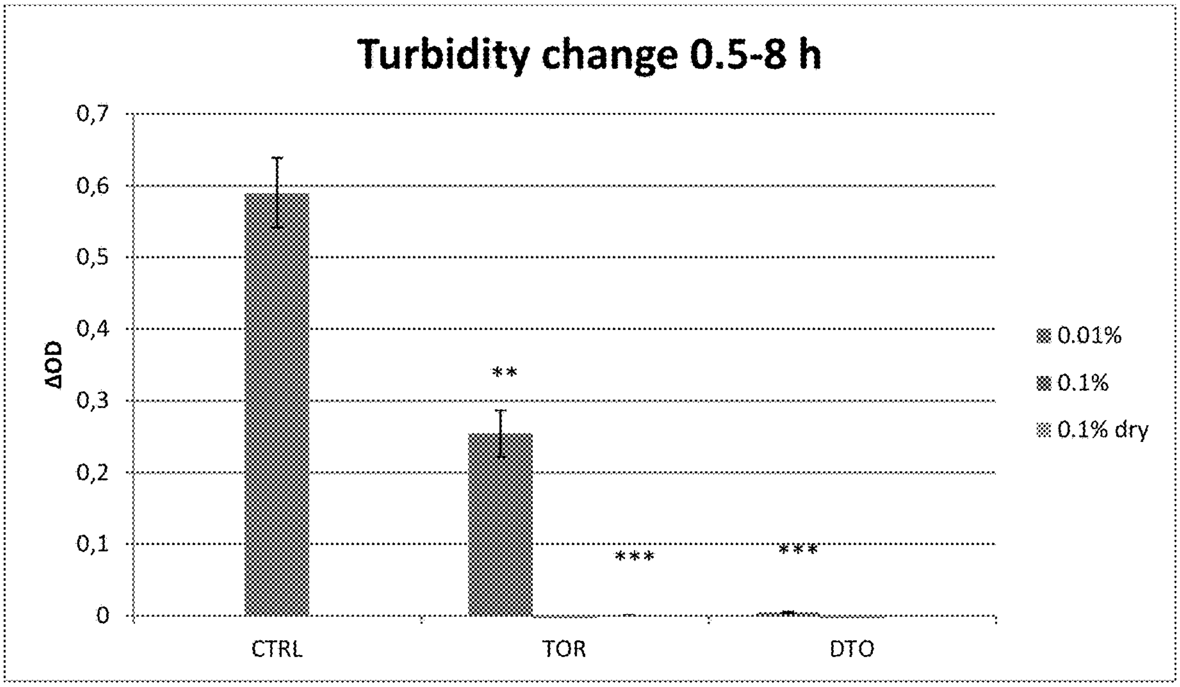
FIG. 1 The turbidity change during 8 hours of *Cl. perfringens* growth as a response to a Tall Oil Rosin (TOR) and Distilled Tall Oil (DTO).

The present invention is based on the realization that a feed supplement which comprises resin acid based composition can be used in the prevention of growth of harmful bacteria in the animal digestive tract, in the modulation of microbial population of the animal digestive tract, in the prevention of intestinal disorders, in enhancing rumen fermentation, lowering rumen methane production and/or in binding toxins.

Resin acids are present in coniferous trees, and there are three main species of resin acid products, namely Tall Oil Rosin (TOR), Wood Rosin and GUM Rosin. TOR is the resin acid fraction separated by vacuum distillation from Crude Tall Oil (CTO) which is produced by the preparation of pulp. CTO is obtained via acidulation of Crude Tall Oil Soap or Crude Sulphate Soap (TOS). TOS is separated from cooking liquid in pulp mill often called black liqueur during pulping process. Wood Rosin is the fraction separated by steam distillation or other means from dead trees, tree stumps, branches etc. and GUM Rosin is the resin fraction that has been steam distilled or separated by other means from resin harvested often called tapping from a living tree.

GUM resin is widely produced in China, Indonesia and Brazil. Wood rosin mainly comes from the USA. TOR is produced in the USA and Scandinavia and to a lesser extent in Central Europe, New Zealand and Russia. Substances containing resin acid and obtained by vacuum distillation from crude tall oil include Distilled Tall Oil (DTO), Tall Oil Fatty Acid (TOFA) and Tall Oil Pitch (TOP). DTO contains 10-40% resin acids. CTO typically contains 15-70% resin acids, and the lowest resin acid contents are generally provided by the cooking of mixed wood pulp.

The term "Tall Oil Rosin" or "TOR" should be understood as referring to a composition obtained by distillation of crude tall oil and further refinement of distilled tall oil. TOR typically comprises 60-99% (w/w) resin acids.

The term "Wood Rosin" should be understood as referring to a composition obtained by distillation or other means from dead trees, tree stumps, branches etc. Wood Rosin typically comprises 50-99% (w/w) resin acids.

The term "GUM Rosin" should be understood as referring to a composition obtained by distillation or separated by other means from resin harvested from a living tree. GUM Rosin typically comprises 50-99% (w/w) resin acids.

The term "Distilled Tall Oil" or "DTO" should be understood as referring to a composition obtained by distillation of crude tall oil and further refinement of distilled tall oil. DTO typically comprises 10-60% (w/w) resin acids.

The resin acid based composition TOR, Wood Rosin, GUM Rosin, CTO, TOS and DTO can also be produced by mixing one or more resin acid compositions and one or more fatty acid compositions in form of oils or fats. Produced resin acid derivatives are for example esters, ethers or alkali metal salts.

Resin acids are known to have antimicrobial, including antibacterial, properties.

The feed supplement or the food supplement of the present invention comprises a resin acid based composition which comprises over 10% (w/w) of resin acids.

In one embodiment of the present invention, the feed supplement consists of a resin acid based composition which comprises over 10% (w/w) of resin acids. In one embodiment of the present invention, the food supplement consists of a resin acid based composition which comprises over 10% (w/w) of resin acids.

In one embodiment of the present invention, the feed supplement comprises or consists of a resin acid based composition which comprises over 12% (w/w) resin acids. In one embodiment of the present invention, the food supplement comprises or consists of a resin acid based composition which comprises over 12% (w/w) resin acids.

The feed supplement or the food supplement is effective for prevention of intestinal disorders, wherein the intestinal disorder is clinical or sub-clinical gastroenteritis, by preventing the collagen breaking activity of matrix metalloproteinases and/or collagen breakdown in the intestinal tissues of an animal or a human, respectively.

In this context, the term "feed supplement" should be understood as referring to a composition that may be added to a feed or used as such in the feeding of animals. The term "feed additive" should be understood, unless otherwise stated, as meaning feed supplement.

In this context, the term "food supplement" should be understood as referring to a composition that may be added to a food or used as such in the feeding of humans.

In this context, the term "feed supplement comprising a resin acid based composition" or "food supplement comprising a resin acid based composition" should be understood as referring to a feed supplement or a food supplement comprising or consisting of the resin acid based composition.

In this context, the term "resin acids" should be understood as referring to a complex mixture of various acidic compounds derived from wood, specially pine wood. They can also be modified resin acids such as dimers and decarboxylated resin acids. The exact composition of the resin acids present in the resin acid based composition varies e.g. according to the species of the trees the composition is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In the context of the feed additive, the resin acid based composition may be any composition described in this specification.

In one embodiment of the present invention the resin acid based composition of the feed supplement comprises at least one of following resin acids abietic acid, dehydoabietic acid, palustric acid, neoabietic acid, pimaric acid and isopimaric acid and/or derivatives thereof. In one embodiment of the present invention the resin acid based composition of the food supplement comprises at least one of following resin acids abietic acid, dehydoabietic acid, palustric acid, neoabietic acid, pimaric acid and isopimaric acid and/or derivatives thereof. The derivatives are obtained by modifying the resin acid chemically, biologically or other ways. In one embodiment of the present invention the resin acid based composition comprises at least one of following resin acids abietic acid, dehydoabietic acid, palustric acid, neoabietic acid, pimaric acid and isopimaric acid. In one embodiment of the present invention the resin acid based composition comprises at least one chemically modified resin acid of abietic acid, dehydoabietic acid, palustric acid, neoabietic acid, pimaric acid and isopimaric acid. The resin acid based composition may also be a mixture of unmodified and modified resin acids.

In one embodiment of the present invention the resin acid based composition of the feed supplement comprises at least three of following resin acids abietic acid, dehydoabietic acid, palustric acid, neoabietic acid, pimaric acid and isopimaric acid and/or derivatives thereof. In one embodiment of the present invention the resin acid based composition of the food supplement comprises at least three of following resin acids abietic acid, dehydoabietic acid, palustric acid, neoabietic acid, pimaric acid and isopimaric acid and/or derivatives thereof.

In one embodiment of the present invention the resin acid based composition is Tall Oil Rosin (TOR).

In one embodiment of the present invention the resin acid based composition and/or TOR comprises over 60% (w/w) resin acids. In one embodiment of the present invention the resin acid based composition and/or TOR comprises over 85% (w/w) resin acids.

The TOR can comprise 32-44.5% abietic acid, 18-25% dehydoabietic acid, 0-3% dihydoabietic acid, 3.0-11.5% isopimaric acid, 0-1.5% 8.5-isopimaric acid, 0-2.5% levopimaric acid, 3.3-4% neobietic acid, 7.5-10% palustric acid, 3-4.5% pimaric acid and 0-4.0% sandaropimaric acid. TOR may comprise <0.1% dimers and 0-7% other components.

In one embodiment of the present invention the resin acid based composition is Wood Rosin.

In one embodiment of the present invention the resin acid based composition and/or Wood Rosin comprises over 10 and up to 99% (w/w) resin acids. In one embodiment of the present invention the resin acid based composition and/or Wood Rosin comprises 50-99% (w/w) resin acids.

The Wood Rosin can comprise 45-51% abietic acid, 7.9-8.5 dehydoabietic acid, 0-1% dihydoabietic acid, 11-15.5% isopimaric acid, 0-4.2% 8.5-isopimaric acid, 0-0.2% levopimaric acid, 4.7-7% neobietic acid, 8.2-10% palustric acid, 3-7.1% pimaric acid and 0-2.0% sandaropimaric acid. Wood Rosin may comprise 0-4.2% dimers and 0-1% other components.

In one embodiment of the present invention the resin acid based composition is GUM Rosin.

In one embodiment of the present invention the resin acid based composition and/or GUM Rosin comprises over 10 and up to 99% (w/w) resin acids. In one embodiment of the present invention the resin acid based composition and/or GUM Rosin comprises 50-99% (w/w) resin acids.

The GUM Rosin can comprise 15-45% abietic acid, 3-15% dehydoabietic acid, 0-0.6% dihydoabietic acid, 3.6-28% isopimaric acid, 0-0.3% 8.5-isopimaric acid, 0-1.8% levopimaric acid, 10-19% neobietic acid, 5-25% palustric acid, 2-7.4% pimaric acid and 0-1.5 sandaropimaric acid. GUM Rosin may comprise 0-1.0% dimers and 0-3.5% other components.

In one embodiment of the present invention the resin acid based composition is Distilled Tall Oil (DTO). In one embodiment of the present invention the resin acid based composition is a distillation fraction of Tall Oil. In one embodiment of the present invention the resin acid based composition is a mixture of DTO and a distillation fraction of Tall Oil. The Distillation fraction of Tall Oil is any resin acids containing fraction of CTO available during CTO refining.

In one embodiment of the present invention the resin acid based composition and/or DTO comprises over 10 and up to 60% (w/w) resin acids. In one embodiment of the present invention the resin acid based composition and/or DTO comprises over 10 and up to 40% (w/w) resin acids.

In one embodiment of the present invention the resin acid based composition is separated from black liqueur during pulping process or TOS or CTO.

The resin acids of the resin acid based composition are insoluble in water. The resin acids of the resin acid based composition may be unmodified or modified.

In one embodiment of the present invention the resin acids of the resin acid based composition and the feed supplement are unmodified. In one embodiment of the present invention the resin acids of the resin acid based composition and the food supplement are unmodified. The term "unmodified" should be understood as referring to the resin acid based composition comprising over 10% (w/w) resin acids that is not modified, i.e. treated chemically, or biologically. The feed supplement or the food supplement comprising or consisting of the resin acid based composition may be used as such.

In one embodiment of the present invention the resin acids of the resin acid based composition are chemically, biologically or other ways modified resin acid compositions. The chemical and/or biological modification of resin acids of the resin acid based composition improves the solubility of its components and resin acids in the digestive tract of an animal. The resin acid based composition may be chemically modified e.g. partially or totally hydrogenated, disportinated, isomerized, oxidized, polymerized, etherified, saponified and/or esterified with suitable compounds, for example, fatty alcohols, glycol, glycerol or glyceridic fatty acid compounds such as mono- di- and tri- and polyglycerides or sugar or polyol based esters. They may be also used as a reactant in Diels-Alder reaction.

In one embodiment of the present invention, the feed supplement comprises a resin acid based composition which is modified by saponification. In one embodiment of the present invention, the food supplement comprises a resin acid based composition which is modified by saponification.

Various processes for the saponification of the resin acid based composition using e.g. NaOH or CaOH are known to a person skilled in the art. In one embodiment of the present invention, the resin acid based composition for use according to the present invention is modified by etherification.

In one embodiment of the present invention the resin acid based composition of the feed supplement comprises 1-90 (w/w) fatty acids and/or their derivatives. In one embodiment of the present invention the resin acid based composition of the food supplement comprises 1-90 (w/w) fatty acids and/or their derivatives. The fatty acids may be in form of oils or fats or in other forms like free fatty acids or esters, ethers or alkali metal salts or fatty alcohols.

In one embodiment of the present invention, the resin acid based composition includes unsaponifiables which have not an acid group, for example, lipophilic neutral substances and esters from wood. In one embodiment of the present invention, the resin acid based composition includes less than 15% unsaponifiables. The amount of unsaponifiables is typically in DTO products less than 5% and in TOR, Wood and GUM Rosin less than 6%.

In one embodiment of the present invention, the feed supplement comprises resin acid based composition which is dried. In one embodiment of the present invention, the food supplement comprises resin acid based composition which is dried. The resin acid based composition can be dried by spray drying, drum drying or by any other known suitable drying method.

In one embodiment of the present invention, the feed supplement comprises different active ingredients. In one embodiment of the present invention, the food supplement comprises different active ingredients.

The feed supplement may be added in the feed in a concentration of 0.0001-10 kg//ton of dry weight of the total amount of the feed. The feed supplement comprising the resin acid based composition according to the invention may be added to the feed, the food or feed supplement as such, or it may in general be further processed as desired.

The food supplement may be added in the food in an amount of 0.05-10 g/day. The food supplement comprising the resin acid based composition according to the invention may be added to the food or food supplement as such, or it may in general be further processed as desired.

The feed supplement or the food supplement comprising resin acid based composition according to the present invention can be modified into a form which is functional and effective in feeds or foods, respectively. Carriers such as oil, fatty acids can be added to the composition for improving the functionality. Further emulgators such as glycerols, lecithin etc. can be added to the resin acid based composition for improving the solubility.

In one embodiment the feed supplement comprising the resin acid based composition according to the present invention may comprise chemically modified resin acid derivatives. In one embodiment the food supplement comprising the resin acid based composition according to the present invention may comprise chemically modified resin acid derivatives. The resin acid derivatives could also comprise rosin based acid anhydrides, dimers, amines, maleimides, alkenyls, epoxy compositions and/or mixtures thereof or with other suitable chemically modified resin acids known to person skilled in the art.

In one embodiment of the present invention, the feed supplement comprises resin acid based composition which is absorbed into a carrier material suitable for the feed composition such as sugarbeet pulp.

In one embodiment of the present invention, the feed supplement comprises resin acid based composition which is mixed with a liquid carrier material suitable for the feed composition such as vegetable oils or fatty acids. In one embodiment of the present invention, the food supplement comprises resin acid based composition which is mixed with a liquid carrier material suitable for the food composition such as vegetable oils or fatty acids.

Further, the feed supplement comprising the resin acid based composition according to the invention may be added to the feed, or it may be administered to an animal separately (i.e. not as a part of any feed composition).

Further, the food supplement comprising the resin acid based composition according to the invention may be added to the food, or it may be administered to a human separately (i.e. not as a part of any food composition).

In this context, the term "feed composition" or "feed" should be understood as referring to the total feed composition of an animal diet or to a part thereof, including e.g. supplemental feed, premixes and other feed compositions. The feed may comprise different active ingredients.

In this context, the term "food composition" or "food" should be understood as referring to the total food composition of a human diet or to a part thereof, including e.g. supplemental food, and other food compositions. The food may comprise different active ingredients.

The present invention also relates to a feed composition comprising the feed supplement according to the invention.

The present invention also relates to a food composition comprising the food supplement according to the invention.

In one embodiment of the present invention, the feed composition comprises the feed supplement in an amount of 0.00001-1.0% (w/w of the dry weight of the total amount of the feed.

In one embodiment of the present invention, the food composition comprises the food supplement in an amount of 0.00001-1.0% (w/w of the dry weight of the total amount of the food.

The present invention also relates to a use of the feed supplement according the present invention in a feed composition.

The present invention also relates to a use of the food supplement according the present invention in a food composition.

The invention also discloses a method of preventing the growth of harmful bacteria in the animal digestive tract, comprising the step of administering to an animal the feed supplement comprising the resin acid based composition according to the invention.

The invention also relates to a method of preventing intestinal disorders, wherein the intestinal disorder is clinical or sub-clinical gastroenteris, by preventing the collagen breaking activity of matrix metalloproteinases and/or collagen breakdown in the intestinal tissues of an animal or a human in need thereof, the method comprising administering to the animal or to the human a feed supplement or a food supplement, respectively comprising a resin acid based composition comprising over 10% (w/w) resin acids.

In the context of this method of preventing intestinal disorders, the feed supplement or the food supplement comprising or consisting of the resin acid based composition may be any composition described in this specification.

In this context, the term "harmful bacteria" should be understood as referring to any bacteria that is capable of affecting the digestive tract or health of an animal or of a human in an adverse manner, including competition for nutrients with the host animal or the human. In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species or humans depending on e.g. the health of an animal or a human and on environmental factors.

In this context, the term "intestinal disorder" should be understood as referring to various disorders of the digestive tract in an animal or in a human, including e.g. diarrhea and other intestinal health problems. The term "clinical or sub-clinical gastroenteritis" should be understood as referring to an inflammation of the gastrointestinal tract—the stomach and small and large intestine. Gastroenteritis can be caused by bacteria, parasites, viruses, mycotoxins, fungus and stress.

Clinical or sub-clinical gastroenteris can be prevented by preventing the collagen breaking activity of matrix metalloproteinases and/or collagen breakdown in the intestinal tissues of an animal or of a human. Animal or human gut is constantly exposed to harmful molecules and microorganisms which endanger the integrity of the intestinal wall. The feed supplement or the food supplement comprising resin acid based composition reduces both duodenal inflammatory T-cell infiltration and small intestinal matrix metalloproteinase (MMP) activity towards collagen type I and type IV. Reduced breakdown of collagen type I and IV indicates a protective effect of resin acids on intestinal barrier integrity by preservation of the basal membrane and the extracellular matrix. The feed additive according to the present invention strengthens intestinal mucosal integrity and promotes intestinal health in animals or humans.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In this context, the term "toxin" should be understood as referring to any poisonous substance produced within living cells or organisms. Toxins are products of plants, animals, microorganisms, for example bacteria, viruses, fungi, rickettsiae, protozoa, etc. In this context, the term "mycotoxin"

should be understood as referring to a toxic secondary metabolite produced by fungi, such as yeast and mould. The most common mycotoxins in grains or silage are for example aflatoxins, zearalenone, ochratoxin A, deoxynivalenol, fumonisin and T-2 toxin. The toxins will vary depending on environmental factors.

In one embodiment of the present invention, the resin acid based composition is administered to an animal in an effective amount.

In one embodiment of the present invention, the resin acid based composition is administered to a human in an effective amount.

The feed supplement comprising the resin acid based composition comprising over 10% (w/w) resin acids is effective in the prevention of growth of harmful bacteria in the animal digestive tract, in the prevention of intestinal disorders, in the modulation of microbial population of the animal digestive tract, in enhancing rumen fermentation, lowering rumen methane production and/or in binding toxins. They have potential in toxin binding.

The present invention has a number of advantages. The feed supplement or the food supplement comprising the resin acid based composition is a readily available, natural, low-cost and environmentally friendly material. Further, it is non-toxic and well tolerated. The feed supplement or the food supplement comprising the resin acid based composition can be used as such. The invention is effective in modulating the composition of the microbiota in the animal or in the human digestive tract to a direction that is beneficial for animal or human performance. Subsequently, other benefits of the invention are e.g. improved animal health and productivity, higher product quality, uniformity, nutritional value and food and product safety, lower costs per production unit and decreased environmental loads. The invention allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

Pathogen Inhibition Test

*Clostridium perfringens* is a pathogenic bacterium that causes necrotic enteritis in broiler chicks and other species of poultry. This experiment was conducted to study the inhibition of *Cl. perfringens* by the resin acid based compositions.

Two resin acid based compositions Tall Oil Rosin (TOR) and Distilled Tall Oil (DTO) obtained from Crude Tall Oil distillation were tested as their efficiency against *Clostridium perfringens* growth. The TOR composition contained 88% (w/w) resin acids and the DTO composition contained 27.5% (w/w) resin acids.

Test Compounds

| Test compounds | |
|---|---|
| TOR (free resin acids 88%) | 0.03 g of 1:1 in turnip rape oil |
| DTO (free resin acids 27.5%) | 0.015 g |
| TOR (free resin acids 88%) | 0.15 ml of 10% stock solution in ethanol |
| DTO (free resin acids 27.5%) | 0.15 ml of 10% stock solution in ethanol |
| TOR (free resin acids 88%) | 0.15 ml of 1% stock solution in ethanol |
| DTO (free resin acids 27.5%) | 0.15 ml of 1% stock solution in ethanol |
| ethanol | 0.15 ml ethanol |

The efficiency of test compositions was tested in a *Cl. perfringens* growth inhibition test that measures both the turbidity of the clostridial culture medium as a result of increased number of bacterial cells in a unit volume of medium, and the cumulative gas production during the simulation.

The efficiency of TOR and DTO against the growth of *Cl. perfringens* was tested at concentrations 0.01%. The TOR with 88% resin acid was melted at +105° C. and mixed 1:1 in turnip rape oil, in order to achieve the same runny form as the other two oily products. This diluted product was dosed as double amount in the simulation.

Simulation procedure: The simulation was conducted in 25-ml glass bottles containing 15 ml of sterile anaerobic TSGY-media (tryptic soy broth-yeast extract media with glucose) and the bottles were enclosed with air-tight stoppers to ensure anaerobic conditions throughout the experiment. At the beginning of the simulation 0.1% inoculums of the overnight grown *Cl. perfringens* culture was injected to TSGY-bottles. Test compounds, or sterile deionized water for the control treatment, were added in a 150 μl final volume from the respective stock solution according to the treatment. The simulation bottles were randomized to avoid artificial bias between treatments. The bottles were kept at an even 37° C. temperature and mixed 1 min before the turbidity measurement at each time point. The total simulation time was 8 h.

The optical density was measured at the time points of 0.5, 4 and 8 hours. The turbidity (optical density, OD) of growth media increases proportionally as the *Cl. perfringens* cell number and cell density increases.

The total gas production was measured at the end of the 8 h simulation as an indicator of growth efficiency, since *Cl. perfringens* produces gas due to the active metabolism during exponential growth.

Results

Figure 2:
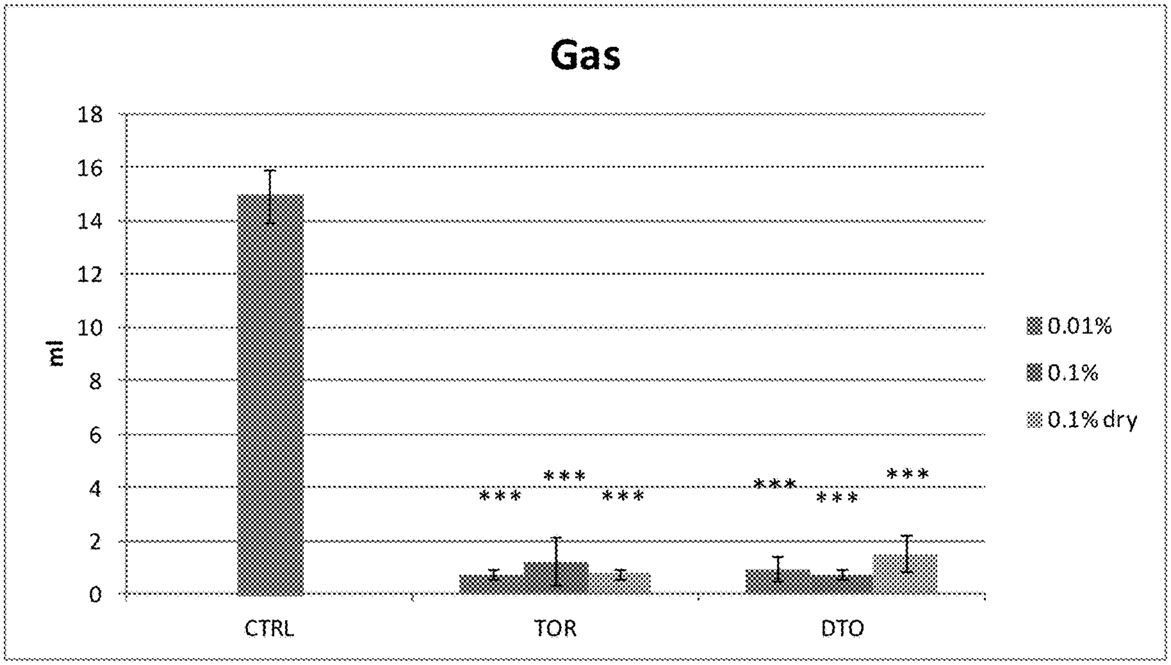
FIG. 2 Gas production during 8 hours by *Cl. perfringens* growth as a response to Tall Oil Rosin (TOR) and Distilled Tall Oil (DTO).

The results are illustrated in FIGS. 1 and 2. The TOR and DTO treatments very effectively inhibited the growth of *Cl. perfringens*, which was detected as the lack of turbidity change (FIG. 1) and the production of negligible amounts of gas (FIG. 2). TOR and DTO compositions inhibited the growth of *Clostridium perfringens* very efficiently regardless of the rosin acid concentration

Example 2

Methane Inhibition Test

Two resin acid based compositions Tall Oil Rosin (TOR) and Distilled Tall Oil (DTO) were tested in methane inhibitio test. The TOR composition contained 88% (w/w) resin acids and the DTO composition contained 27.5% (w/w) resin acids. The TOR composition containing 88% (w/w) resin acids was mixed 1:1 with turnip rape oil.

The methane inhibition test was conducted with rumen-fistulated dairy cows in order to study the potential of TOR and DTO to decrease the rate of methane production in the rumen. Rumen fluid samples were measured for the numbers of methanogenic bacteria, as they are the methane-producing organisms. The short chain fatty acid profiles, including the concentration of branched chain fatty acids, of the samples were measured as they indicate whether resin based acid compositions had effects to ruminal fermentation.

Three rumen-fistulated, lactating dairy cows were given 3.0 g of dry test compositions/head/day for 21 days, in four portions. TOR and DTO compositions were first dried onto sugar beet pulp and then mixed into the compound feed. Rumen samples were taken before the dietary intervention, once a week during the test composition feeding, and after a two-week washout period. The samples of the trial were analysed for short chain fatty acids (SCFAs) by gas chromatography and numbers of methanogens, protozoa and total bacteria by qPCR.

Results

The results show that the numbers of methane producing bacteria decreased numerically during the TOR and DTO feeding period, while protozoa and the total number of bacteria were not affected by the product. The levels of lactic, propionic, and valeric acids and total short chain fatty acids tended to decrease in the rumen fluid during the TOR and the DTO feeding period. The concentration and relative proportion of branched chain fatty acids tended to decrease as a response to TOR and the DTO.

The experiment shows that the TOR and the DTO lowers the amount of methanogens and thus lowers rumen methane production. The experiment also shows that the TOR and the DTO enhances rumen fermentation.

Example 3

This experiment was conducted to study the effect of saponified DTO with 35% (w/w) resin acids with or without Sugar Beet Pulp (SBP) carrier on the microbial microbial population and fermentation of broiler chick ileum in vitro.

The saponified DTO was manufactured by adding NaOH (sodium hydroxide) to DTO, adding enough water to adjust the total dry matter (DTO) percentage of the mixture to 18-20%, heating the mixture to +90° C., keeping the temperature at +90° C. for 120 minutes, during which time the mixture was gently stirred at 15 min intervals.

Experiment

Ileal contents of 40-days old broiler chicks were used for the simulation media and as inoculants in the simulation models. The trial treatments were prepared from a batch of saponified DTO.

Preparations of DTO with 35% resin acids were produced:

1. Saponified DTO with 20% dry matter content

An aliquot of the DTO soap was heated to 90° C., mixed with finely ground SBP powder, and dried.

2. Saponified DTO

Gastrointestinal digestion of the saponified DTO: Part of the liquid DTO soap and the carrier-absorbed DTO soap was digested by a pepsin-HCl—treatment (pH 2.25) followed by a pancreatin bile-acid-NaOH treatment (pH 6.2) in a dilution series. The digestion was made to evaluate whether the products would resist the conditions of the upper gastrointestinal tract before they enter the distal intestine with higher microbial activity.

The simulation was conducted in a total of 160 2-ml plastic microcentrifuge vials, in 1.5 ml volume, with 10 hours simulation time. Samples were tested at four concentrations of the dry matter of DTO: 0%, 0.005%, 0.01%, 0.01% and 1%.

All the simulation samples were analysed for short chain fatty acids and the total number of microbes. In addition, selected samples were analysed for a number of microbial species or groups by quantitative real-time PCR (qPCR). Ileal simulation samples were analysed for lactobacilli and streptococci.

Results

In the ileal simulation model, DTO soap at 0.5 kg/ton level increased the concentrations of acetic and propionic acids and decreased the concentration of lactic acid. This suggests modulation of microbial metabolism from homofermentative towards heterofermentative metabolical route, which can be seen as a very positive change improving the feed conversion ratio. The sugar beet pulp carrier had little effect on the fermentation

Example 4

Test A: Toxin Adsorption into Solid Phase In Vitro

The capacity of a test product to remove toxins from aqueous medium was measured in this test. An efficient toxin adsorbent should be able to bind the toxin in all compartments of the digestive tract, to inhibit the toxin from getting absorbed by the animal. To evaluate the efficacy of the binder in the acidic stomach, the test was run at pH value 2.5 (50 mM glycine-HCl buffer).

The test product was a saponified DTO product which contains 20% resin acids. The saponified DTO was manufactured as in example 3. The product tested was the saponified DTO (20%) with or without silicate carrier.

The test A was conducted with two toxins Ochratoxin A (OTA) and Zearalenone (ZEA), at pH-value 2.5, three test substance levels 0.2, 0.5 and 1 kg/ton and four replicate samples per treatment. Control treatment was replicated 8 times.

Mycotoxins OTA and ZEA were available as 3H-labeled pure compounds, and radioactivity, measured by liquid scintillation counting, was used for their quantification in the samples.

The experiment was conducted in silanized glass vials in 1 ml volume of buffer. In the test system, the bound radioactive toxin becomes removed from the liquid phase through co-pelleting with the insoluble components of the potential binder. The following procedure was used: 1. The test products were weighed into the vials, 2. 3H -labeled and intact mycotoxin was mixed with the buffers to get the final toxin concentration of 10 μg/l, 3. 1 ml of the buffer-mycotoxin solution was added to the vials, 4. The vials were sealed and kept for 2 hours at 37° C. in constant slow shaking, 5. The vials were centrifuged for 10 min at 3000×g 6. 50 μl of the supernatant was mixed with 150 μl of liquid scintillation cocktail (Optiphase) into wells of a 96-well microtiter plate and 7. The radioactivity of the samples was measured with a liquid scintillation counter for five minutes Results The saponified DTO was able to bind OTA from the aqueous medium statistically significantly, and the binding was dependent on the concentration of the test product. The saponified DTO adsorbed 25-60% of the free OTA from the medium.

The saponified DTO significantly decreased the amount of free ZEA even at the lowest dosages. The saponified DTO removed approximately 30-60% of the free toxin.

Example 5

This experiment was conducted to study the effect of dietary supplementation of resin acid based composition comprising 98.6% resin acids on broiler intestinal health under non-challenged conditions. The experiment focused on the effect of resin acids on collagenolytic activities, since host metalloproteinases involved in collagen breakdown are known to play a crucial role in maintaining intestinal mucosal structure. The resin acid based composition used in this study represents the pure resin acid fraction which contains mainly abietic acid and dehydroabietic acid as shown in Table 1.

TABLE 1

The resin acid composition

| Major resin acids | w % |
|---|---|
| abietic acid | 47.30 |
| dihydroabietic acid group | 1.80 |
| dehydroabietic acid | 22.60 |
| neoabietic acid | 0.90 |
| dehydrodehydroabietic acid | 0.80 |
| 7,9 (11)-abietic acid | 5.30 |
| 13-B-7,9 (11)-abietic acid | 4.50 |
| 8,12-abietic acid | 1.90 |
| 8,15-pimaric acid | 1.40 |
| pimaric acid | 0.50 |
| isopimaric acid | 3.40 |
| sandaracopimaric acid | 1.40 |
| palustric acid | 6.80 |

Experiment

Twenty, one-day-old Ross 308 broilers were housed in two pens (10 chickens per pen) on wood shavings. Water and commercial starter feed containing wheat, soy, corn, rice bran, wheat gluten, soy oil, corn gluten, palm oil, calcium carbonate, monocalcium phosphate, corn bran, sodium chloride, sodium bicarbonate (day 1-10) or grower feed containing wheat, soy, corn, wheat gluten, sunflower seeds, soy oil, palm oil, calcium carbonate and monocalcium phosphate (day 11-22) were provided ad libitum. The control group received the standard non-supplemented diet, whereas the birds in the treatment group were fed the same feed supplemented with 200 mg resin acid composition/kg feed throughout the whole trial period. Upon arrival (day 1) and on days 7, 14 and 22 all birds were weighed. At day 22, all birds were 119 euthanized for sampling. Intestinal tissue from the different segments of the small intestine was snap frozen in liquid nitrogen and stored at −20° C. until protein extraction was performed for MMP analysis. Additionally, duodenal and ileal tissue samples were collected and fixed in 4% phosphate buffered formaldehyde for histological analysis.

CD3 Immunohistochemistry

Slides for immunohistochemical staining for CD3+ cells were automatically deparaffinized (Shandon Varistain-Gemini) before antigen retrieval with a pressure cooker in citrate buffer (10 mM, pH 6). Endogenous peroxidase activity was blocked by treating the slides with peroxidase blocking reagent (S2023, Dako, Glostrup, Denmark) for 5 minutes. The presence of T-cells (CD3-positive cell abundance) in intestinal tissue from both duodenum and ileum was evaluated using polyclonal primary antibodies against CD3 (A0452, Dako, 1:100 dilution, 30 min at room temperature), followed by incubation with a secondary labelled polymer-HRP anti-rabbit (Envision+ System-HRP (DAB) (K4011), 30 min at room temperature). Slides were evaluated using the computer based image analysis program, LAS V4.1. The CD3+ area percentage in either the duodenal or ileal tissue was quantified using three representative fields of view per intestinal section.

Intestinal Tissue Lysates

Proteins were extracted from the small intestinal tissue (duodenum, jejunum and ileum) using mechanical lysis. In brief, intestinal tissues (~30 mg) were homogenized in 400 μl TBS-1% NP-40 (50 mM Tris/HCl, pH 8.0, 150 mM NaCl and 1% (v/v) NP-40, supplemented with EDTA-free protease inhibitor cocktail (Complete, Roche, Mannheim, Germany)) by grinding (2×) with a combination of 2.3 mm zircon/silica and 3.2 mm stainless steel beads (BioSpec Products, Bartlesville, OK, USA) in a bead beater (1.5 min, 22.5 Hz; TissueLyser) with a 30 sec interval between shakings. Samples were centrifuged for 10 min at 8000 rpm and the supernatant was transferred to a new tube. Protein concentration was measured using the BCA protein assay (Thermo Fisher Scientific) and samples were stored at −20° C. until further analysis.

EnzChek Gelatinase/Collagenase Assay

The Molecular Probes EnzChek® Gelatinase/Collagenase Assay Kit was used to evaluate the breakdown of gelatin, collagen type I and collagen type IV by enzymes present in the small intestinal tissues (jejunum or ileum). These substrates were labeled with fluorescein and a quenching agent. Duplicate measurements were performed in 200 μl reaction volume containing 20 μl of either fluorescein labelled substrate (DQ Collagen I (25 μg/ml, D12060), DQ Collagen IV (25 μg/ml, D12052), or DQ Gelatin (12.5 μg/ml, D12054)), 100 μl of the tissue lysate (500 μg/ml) and 80 μl of reaction buffer (0.5 M Tris-HC1, 1.5 M NaCl, 50 mM CaCl2 and 2 mM sodium azide with pH 7.6). Samples were incubated for 10 h at room temperature in the absence of light, after which fluorescence was measured (excitation 485 nm, emission 527 nm; Fluoroskan Ascent Fluorometer, Thermo Fisher Scientific Inc., Waltham, USA). Background fluorescence was subtracted for each sample.

Gelatin Substrate Zymography

Gelatin zymography was used to identify the gelatinolytic enzymes in the ileal tissue lysates. Polyacrylamide gel (10%) containing 0.2% gelatin (2 mg/ml) as substrate was used for determination of MMPs gelatinolytic activity. Equal concentrations of ileal tissue lysates from the resin acid based composition-supplemented birds or control birds were pooled, after which 10 μl pooled ileal tissue lysate (1 mg/ml) was mixed with 10 μl 2× loading buffer (0.5M Tris-HCl pH 6.8, 20% glycerol, 4% SDS, a pinch of bromophenol blue) and loaded to the gel. After standard electrophoresis, the gel was incubated with renaturing buffer (2.5% Triton X-100, 30 minutes, room temperature) to remove SDS from the gel. This allows the enzymes in the gels to renature and autoactivate. The gel was washed with developing buffer (150 mM NaCl, 5 mM CaC12, 0.05% NaN3 and 50 mM Tris-HCl buffer pH 7.5) and incubated with fresh developing buffer under continuous shaking at 37° C. for 18 hours. After incubation, the gel was stained with Coomassie brilliant blue (Sigma-Aldrich). Activity of gelatin-degrading enzymes is visualized as colorless bands on a blue background. Gel images were analyzed with a GS-800 calibrated densitometer and the Quantity One software (BioRad, Hercules, CA, USA).

Statistical Analysis

A students t-test was used for normal distributed data. When the data were not normally distributed, the comparisons between groups were done by Mann-Whitney U test.

Analyses were done with 95% confidence intervals and significance was determined as $P \leq 0.05$.

Results

Body Weight

Broilers receiving a diet supplemented with resin acid based composition did not present significant differences in body weight as compared to controls. No mortality was observed during the study.

Resin Acid Based Composition Reduce Duodenal T-Cell Abundance

The amount of CD3+ T-cells was determined in both the ileal and duodenal tissue as a marker for intestinal inflammation. No changes in ileal T-cell abundance were observed, whereas the amount of CD3+ positive cells in the duodenal tissue from birds fed the resin acid based composition-supplemented diet was significantly decreased as compared to the control birds as shown in Table 2.

TABLE 2

Effect of resin acid based composition-supplementation on T-cell abundance of chickens on day 22

| | Diet | | |
|---|---|---|---|
| | Control | Resin acids | P-value |
| | CD3 area percentage | | |
| Duodenum | 6.78 ± 2.12 | 4.78 ± 1.62 | 0.036 |
| Ileum | 14.54 ± 4.05 | 12.24 ± 4.88 | 0.27 |

Figure 3A:
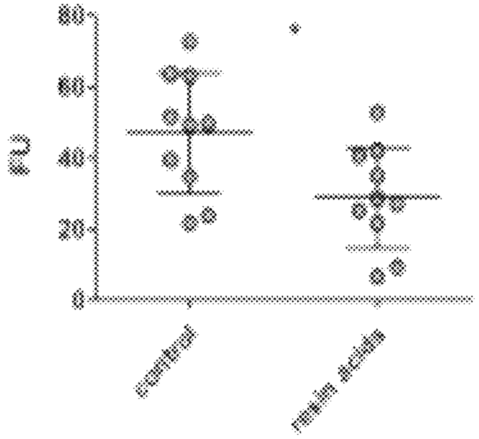
FIG. 3A Relative gelatin degrading activity present in jejunal from control birds and birds fed the resin acid based composition-containing diet.
Figure 3B:
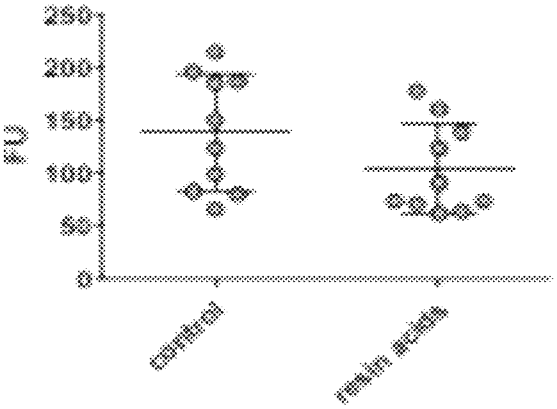
FIG. 3B Relative collagen type I degrading activity present in jejunal from control birds and birds fed the resin acid based composition-containing diet.
Figure 3C:
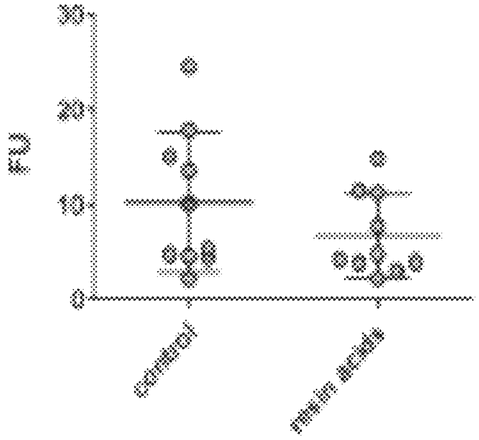
FIG. 3C Relative collagen type IV degrading activity present in jejunal from control birds and birds fed the resin acid based composition-containing diet.
Figure 3D:
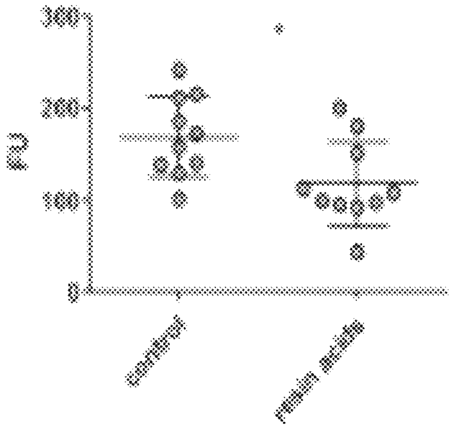
FIG. 3D Relative gelatin degrading activity present 789 in ileal from control birds and birds fed the resin acid based composition-containing diet.
Figure 3E:
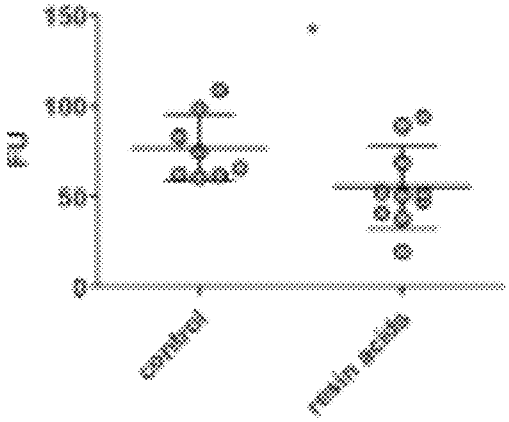
FIG. 3E Relative collagen type I degrading activity present in ileal from control birds and birds fed the resin acid based composition-containing diet.
Figure 3F:
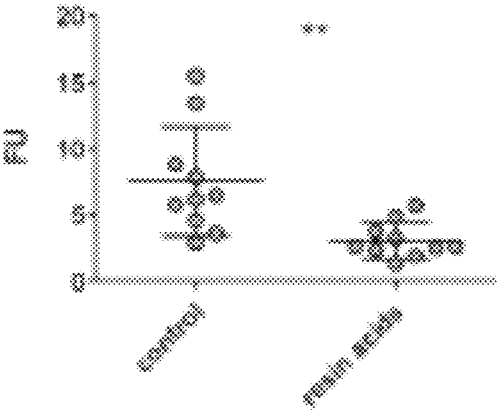
FIG. 3F Relative collagen type IV degrading activity present in ileal from control birds and birds fed the resin acid based composition-containing diet.

Resin Acid Based Composition-Supplementation Decreases the Collagenolytic Activity in the Broiler Ileal Tissue The enzymatic activity towards gelatin, collagen type I or collagen type IV present in the small intestinal tissue was assessed as a measure for extracellular matrix degradation in the gut. Jejunal (A-C) or ileal (D-E) intestinal tissue lysates from either control birds or resin acid based composition fed birds were incubated for 10 hours with fluorescently labelled gelatin (A and D), collagen type I (B and E) or collagen type IV (C and F). The results are illustrated in FIGS. 3A-F. In the FIGS. 3 FU is relative fluorescence unit after 10 h incubation, control birds are cotrol and resin acid based composition fed birds are resin acids. Breakdown of the fluorescently labelled substrate results in an increase of fluorescence which is proportional to the substrate degrading activity of the sample. In the jejunum, significantly lower gelatinase activity was measured in the tissue from resin acid based composition fed birds as compared to the control group (FIGS. 3A-C). The biggest effect of resin acids was observed in the ileal tissue, where gelatin, collagen type I and collagen type IV degrading activity was significantly decreased by supplementation of resin acid based composition to the broiler feed (FIGS. 3D-F).

Figure 4:
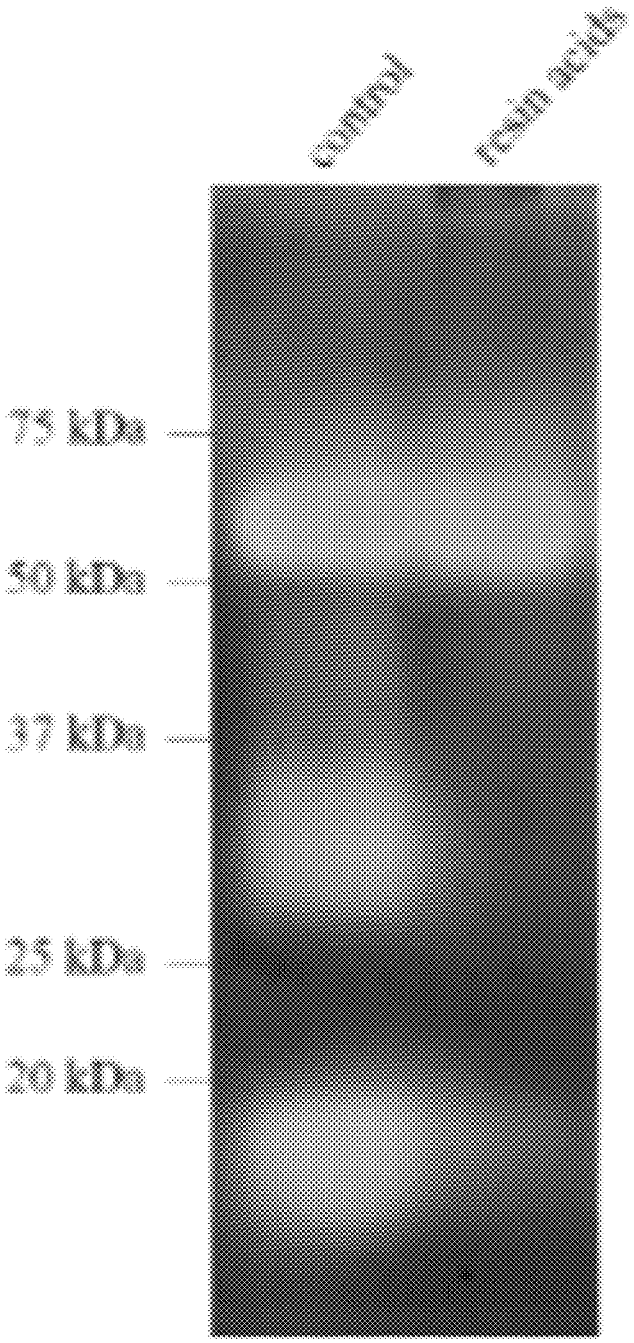
FIG. 4 Effect of resin acid based composition-supplementation on ileal gelatinolytic enzymes.

To gain more information on the identity of the enzymes, pooled ileal tissue lysates were subjected to gelatin zymography. The results are illustrated in FIG. 4. The ileal tissue from the control birds (control) showed three different gelatinolytic bands, whereas in the ileal tissue from the resin acid based composition group (resin acids), only the highest molecular weight enzyme was present. The two enzymatic bands that were exclusively detected in the ileum from control birds correspond to MMP7 (~18 kDa) and its latent pro-388 enzyme forms (pre-proMMP7: ~30 kDa and proMMP7: ~28 kDa) (UniprotKB: F6R1W4_CHICK). FIG. 4 shows that enzyme MMP7 was missing in the ileal tissue from the resin acid based composition group.

The results show that administration of resin acid composition to broiler feed has a major effect on the host intestinal tissue. The dietary resin acid composition supplementation resulted in decreased abundance of inflammatory T-cells in the duodenal tissue and reduced matrix metalloproteinase (MMP) activity, while maintaining optimal intestinal morphology. MMPs are zinc-dependent endopeptidases that are able to degrade extracellular matrix molecules as well as other molecules that are important within the mucosal layer, such as, amongst others, membrane receptors, adhesion factors, signaling molecules and cytoskeleton proteins. MMPs are involved in various enteric inflammatory diseases, such as inflammatory bowel disease and necrotic enteritis in broilers. The most profound effect of resin acid based composition supplementation on MMP activity was observed in the ileum, resulting in a reduction of both collagen type I and collagen type IV degrading activity. Both collagen subtypes are important for the structural integrity of the intestinal wall. Collagen type I is a major supportive component of the extracellular matrix, whereas type IV collagen is an integral component of the basement membrane supporting the epithelial cells. The main enzyme responsible for the reduced collagenolytic activity in the resin acid based composition had a molecular weight corresponding to both the latent and active forms of MMP7. In the healthy intestine, various MMPs are expressed, but the production of MMP7 is mainly linked to injured epithelium. MMP7 can disrupt epithelial barrier integrity by degrading intercellular junction molecules such as cadherins and occludins. Furthermore, MMP7 is able to activate α-defensins by cleaving its precursor into the active form. Alpha defensins are antimicrobial peptides that are secreted by epithelial cells and granulocytes, which play a role in protection of the host against microbial invasion during intestinal inflammation and can induce IL6 secretion by macrophages, thereby contributing to intestinal leakage and inflammation. As the broiler gut is continuously exposed to various challenges that affect intestinal barrier integrity and can trigger inflammation (e.g. coccidia, mycotoxins, bacterial toxins, amongst others) reducing MMP7 activity through resin acid based composition-supplementation to the diet supports animal performance by enhancing intestinal barrier integrity and controlling inflammation in the avian gut.

The resin acid based composition-supplementation of broiler diet reduced duodenal inflammatory T-cell abundance and small intestinal MMP activity.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method for preventing intestinal disorders, wherein the intestinal disorder is clinical or sub-clinical gastroenteritis caused by bacteria, by preventing the collagen breaking activity of matrix metalloproteinases and/or collagen breakdown in the intestinal tissues of an animal or a human in need thereof, the method comprising administering to the animal or to the human a feed supplement or a food supplement, respectively, comprising an effective amount of a resin acid based composition comprising over 12% (w/w) resin acids.

2. The method according to claim 1, wherein the resin acid based composition comprises at least one of following: abietic acid; dehydoabietic acid; palustric acid; neoabietic acid; pimaric acid; isopimaric acid; or derivative thereof.

3. The method according to claim 1, wherein resin acid based composition comprises at least three of following: abietic acid; dehydoabietic acid; palustric acid; neoabietic acid; pimaric acid; isopimaric acid; or derivative thereof.

4. The method according to claim 1, wherein resin acid based composition comprises Tall Oil Rosin (TOR), Wood Rosin, GUM Rosin, Distilled Tall Oil (DTO), or mixture thereof.

5. The method according to claim 1, wherein resin acid based composition consists of Tall Oil Rosin (TOR), Wood Rosin, GUM Rosin, Distilled Tall Oil (DTO), or mixture thereof.

6. The method according to claim 1, wherein the resin acid based composition comprises Tall Oil Rosin (TOR).

7. The method according to claim 1, wherein the resin acid based composition comprises over 60% (w/w) resin acids.

8. The method according to claim 1, wherein the resin acid based composition comprises Wood Rosin or GUM Rosin.

9. The method according to claim 8, wherein the resin acid based composition comprises over 10 and up to 99% (w/w) resin acids.

10. The method according to claim 1, wherein the resin acid based composition comprises Distilled Tall Oil (DTO).

11. The method according to claim 10, wherein the resin acid based composition comprises over 10 and up 60% (w/w) resin acids.

12. The method according to claim 1, wherein the resin acids are unmodified.

13. The method according to claim 1, wherein the resin acid based composition is absorbed into a carrier or mixed with a carrier.

* * * * *